US00PP31602P3

(12) United States Plant Patent
Hansen

(10) Patent No.: US PP31,602 P3
(45) Date of Patent: Mar. 24, 2020

(54) ***SALVIA* PLANT NAMED 'BUMBLEBERRY'**

(50) Latin Name: ***Salvia nemorosa* (Linnaeus)**
Varietal Denomination: Bumbleberry

(71) Applicant: Hans A. Hansen, Zeeland, MI (US)

(72) Inventor: Hans A. Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 15/731,913

(22) Filed: Aug. 22, 2017

(65) Prior Publication Data

US 2019/0069466 P1 Feb. 28, 2019

(51) Int. Cl.
*A01H 5/02* (2018.01)

(52) U.S. Cl.
USPC ..... Plt./475
CPC ..... *A01H 5/02* (2013.01)

(58) Field of Classification Search
USPC ..... Plt./475
See application file for complete search history.

*Primary Examiner* — Anne Marie Grunberg

(57) ABSTRACT

The new and distinct cultivar of perennial *Salvia* plant named 'Bumbleberry' characterized by its small strong purplish red-colored flowers densely arranged in verticils, with compact rounded habit and stiff, upright, heavily-branched stems and strong vigorous growth rate and small gray-green foliage. *Salvia* 'Bumbleberry' is winter-hardy and especially useful for landscaping and containerized ornamentals by itself or in combination with other plants.

1 Drawing Sheet

Botanical denomination: *Salvia nemorosa* (Linnaeus).
Cultivar designation: 'Bumbleberry'.

BACKGROUND OF THE INVENTION

The present invention relates to a new and distinct cultivar of ornamental sage plant hereinafter referred to by the cultivar name *Salvia* 'Bumbleberry' or as the new plant. The new plant was the result of an insect pollination of the proprietary, unreleased, non-patented hybrid known as 12-98-1 times a sibling of 12-98-1 as part of the hybridizing program at a wholesale perennial nursery in Zeeland, Mich., USA in late spring of 2013. The seeds from the cross were harvested mid-summer of 2013 and the single specific seedling that developed into the new *Salvia* was assigned the breeder code 13-64-12 at the end of the evaluation process at the same nursery in the summer of 2015. The first asexual propagation was performed in the summer of 2015 by shoot tip cuttings at the same nursery in Zeeland, Mich. 'Bumbleberry' has proven that it is stable and reliably produces true to type plants in successive generations of asexual propagation.

No plants of *Salvia* 'Bumbleberry' have been sold or disclosed in this country, or anywhere in the world, by this or any name, more than one year prior to the filing of this application, with the exception of that which was sold or disclosed either directly or indirectly from the inventor and within one year from the filing of this application.

SUMMARY OF THE INVENTION

Plants of *Salvia* 'Bumbleberry' have not been observed under all possible environmental conditions. The phenotype may vary somewhat with variations in environment such as temperature, nutrition and light intensity without, however, any variance in genotype.

*Salvia* 'Bumbleberry' can be most closely compared to 'Sensation Rose' U.S. Plant Pat. No. 18,230. The new plant is slightly taller in habit, the foliage is larger and the flower is a strong purplish red rather than light purple to light reddish purple. Comparison with the specific female parent is not possible as the female was not retained. Comparison with the possible male parent, is not possible as the exact male parent is now known or maintained. Compared with 'May Night' (not patented), the new plant has more purplish red-colored flowers and more compact habit and lower height.

The following characteristics in combination distinguish *Saliva* 'Bumbleberry' as a new and distinct cultivar:

1. Small, strong purplish red-colored flowers densely arranged in tight verticils;
2. Compact rounded habit and stiff, upright, heavily-branched stems;
3. Strong, vigorous and winter-hardy;
4. Small, rugose, gray-green foliage.

BRIEF DESCRIPTION OF THE DRAWINGS

The photographs of the new plant demonstrate the unique traits and the overall appearance of *Salvia* 'Bumbleberry'. The colors are as accurate as reasonably possible with color reproductions. Variation in ambient light spectrum, source and direction may cause the appearance of minor variation in color. The plant used in the photographs was a two-year old plant grown in an open, full-sun trial garden at a wholesale perennial nursery in Zeeland, Mich. with supplemental water and fertilizer when needed. No stem pinching or plant growth regulators have been used.

DETAILED BOTANICAL DESCRIPTION

Figure 1:
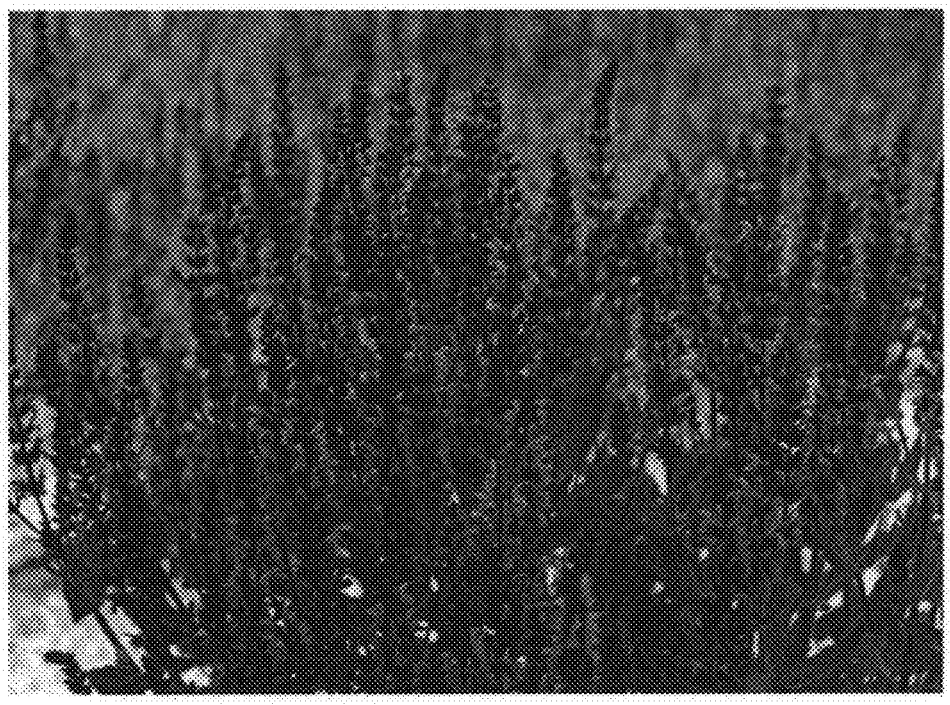
FIG. 1 shows the plant habit in full flower in a landscape.
Figure 2:
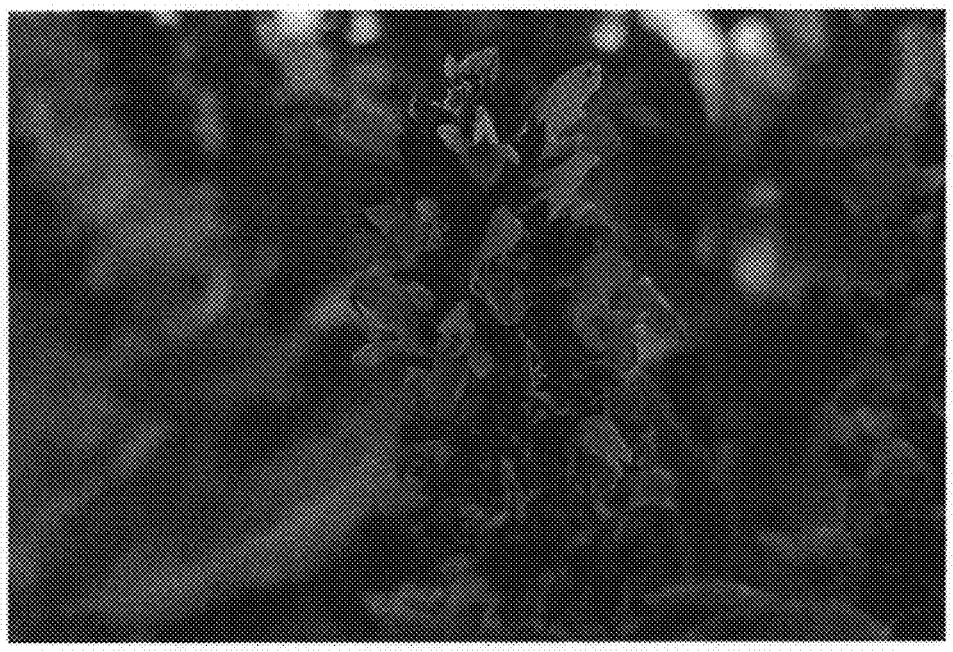
FIG. 2 shows a close-up of the flower scape with the buds and unique strong purplish red color.

The following descriptions and color references except where common dictionary terms are used are based on the 2015 edition of The Royal Horticultural Society Colour Chart. *Salvia* 'Bumbleberry' has not been observed under all possible environments. The phenotype may vary slightly with different growing environments such as temperature, light, fertility, soil pH, moisture and plant maturity levels, but without any change in the genotype. The following observations and size descriptions are based on two-year old plants growing in an outdoor full-sun trial garden at a wholesale perennial nursery in Zeeland, Mich. Plants were given supplemental water and fertilizer but no plant growth regulators were used.

Botanical classification: *Salvia nemorosa* (Linnaeus);

Parentage: Female or seed parent is the unreleased non-patented proprietary hybrid known as 12-98-1; the male or pollen parent was a non-patented proprietary sibling of 12-98-1; the proprietary hybrids were both offspring of a cross of 'Sensation Rose' and 'May Night';

Plant habit: Winter-hardy herbaceous perennial; multi-stemmed, compact, with basal and cauline foliage, and flowers in several tightly arranged verticils on heavily-branched upright racemes displayed above foliage; flowering in panicles about 30.0 cm tall and about 40.0 cm wide at the fullest point about 18.0 cm above soil; foliage extends about two-thirds of the way up the stems;

Propagation: By herbaceous tip cuttings; time to produce a rooted stems about two weeks;

Growth rate: Rapid, vigorous, finishing in from a 25 mm plug to flower in one-gallon pot in about 10 to 12 weeks, and flowering in a one-gallon pot from a dormant bare-root one-year-old plant in about 6 to 8 weeks;

Root description: Fine, well-branched; color dependent on age and soil type, from cream to dark tan in color;

Foliage: Opposite, simple, rugose, ovate; glabrous to sparsely puberulent abaxial and glabrous adaxial; acute apex and base cordate to rounded; margin crenate; leaf blades about 9.4 cm long and 3.5 cm across, decreasing in size distally; average about 7.5 cm long and 2.6 cm across;

Foliage fragrance: Faint sage fragrance;

Foliage color: Mature adaxial surface nearest RHS 137A, mature abaxial surface between RHS 147B and RHS 146A; expanding adaxial base nearest RHS 144A and distally nearest RHS 137B, expanding abaxial nearest RHS 138B;

Venation: Reticulate; impressed on adaxial side and ribbed on abaxial side; puberulent abaxial and glabrous adaxial;

Vein color: Mature adaxial midrib nearest RHS 145D with main and secondary veins nearest RHS 147D near midrib and becoming nearest RHS 137A distally, and mature abaxial midrib and main veins nearest RHS 145C; expanding adaxial midrib nearest RHS 148D with main and secondary veins nearest RHS 194A and expanding abaxial midrib RHS 148C with main and secondary veins nearest RHS 148C;

Petiole: Concavo-convex, ciliate along margin and sparsely puberulent abaxial and adaxial surfaces; to about 4.5 cm long and 4.0 mm wide at base, average 3.2 cm long and 3.5 mm wide at base;

Petiole color: Adaxial center nearest RHS 145C and margins nearest RHS 137C; abaxial center nearest RHS 145C and margins nearest RHS 137C;

Stems: Quadrangular; pubescent, to 5.0 cm long before flowers and 4.5 mm across at base;

Stem color: Nearest RHS 138A;

Nodes: Eight before flowering verticils; average internode length 6.3 mm; color same as stem;

Flower: Perfect; bilabiate; zygomorphic; verticillate with flowering generally beginning at lower verticils and advancing up the scape, not all flowers at same verticil opening at the same time; with lower lip projected downward almost vertically and parallel to stem and hood petal upwardly at about 45 degree angle above horizontal; self-cleaning, petals not persistent; flowering beginning late spring for about four weeks and repeating if initial scapes removed;

Flower longevity: About four days on the plant or as cut flower;

Flower fragrance: None detected;

Flower buds one to two days prior to anthesis: Ellipsoidal with narrow basal tube, rounded apex; exposed petals puberulent; calyx carinate and micro puberulent; about 8.0 mm long, 2.5 mm tall and 1.5 mm wide;

Flower bud color: Exposed petals nearest RHS 64A; calyx top nearest RHS 187B and below RHS 146D, calyx veins nearest RHS 187B;

Flowers size: About 13.0 mm long from base of calyx to tip of exserted style, 8.5 mm tall and 5.5 mm wide; clustered at verticils with about six flowers per verticil;

Petals: Bilabiate corolla; upper hood projecting upwardly to about 45 degrees from horizontal and lower labium drooping producing an angle between the two petals of about 90 degrees;

Hood (upper) petal: Slightly arcuate to falcate in distal half; vertically conduplicate in distal 7.0 mm, with emarginate apex and basal 6.0 mm fused into tube 2.0 mm diameter at base and 3.0 mm diameter at petal separation; puberulent abaxial, glabrous adaxial; 13.0 mm long, 3.0 mm tall and 1.0 mm across;

Labium (lower) petal: Abaxial puberulent, glabrous adaxial; consisting of three apical lobes, two upwardly projecting lateral lobes about 2.0 mm long and 1.5 mm wide at base, each lobe with rounded apex; one central, obdeltoid, distally involute lobe about 3.5 mm long 6.0 mm wide with rounded apex; about 10.0 mm long fused into tube in basal 6.0 mm, 5.0 mm wide at the widest portion and 2.5 mm tall;

Petal color: Abaxial hood between RHS 71D and RHS 70B; adaxial hood nearest RHS 72D; labium central lobe adaxial nearest RHS 77A and abaxial nearest RHS N80A; labium side lobes adaxial nearest RHS NN74C and abaxial nearest RHS NN74D; fused base abaxial proximal region nearest RHS N155B, distal dorsal side lighter than RHS 70D and ventral side nearest RHS 85A; adaxial tube distally nearest RHS 84D ventral and lighter than RHS 75D dorsally with base nearest RHS N155B;

Androecium: Two, with diminutive trigger mechanism; fused with labium, contained within hood petal;

*Filaments*.—Two; adnate to petal about 4.0 mm from base and curved downward inside hood petal; glabrous; about 3.0 mm long and about 0.2 mm diameter; adnate about 4.0 mm from base of labium petal; color nearest RHS 76D.

*Anther*.—Glabrous, ellipsoidal; about 1.0 mm long and about 0.5 mm diameter; longitudinal, dorsifixed; color blend nearest RHS N77C.

*Pollen*.—Globose, less than 0.5 mm circumference; color nearest RHS 8C.

*Trigger mechanism*.—About 1.0 mm long, curved; color nearest RHS 76D.

Gynoecium: One, curved around inside of hood petal; total about 1.2 cm long;

*Style*.—About 9.0 mm long and less than 0.5 mm diameter; color nearest RHS NN155C at base, darkening distally to nearest RHS N82A before stigma split.

*Stigma*.—Bifid curved in the terminal 1.5 mm; apex pointed; color nearest RHS 83C.

*Ovary*.—Superior; about 1.0 mm diameter; color nearest RHS 145A.

*Fruit*.—One to four nutlets per flower; ellipsoidal to spherical; about 1.0 mm diameter; color nearest RHS 202A.

Calyx: Five sepals; three upper and two lower, campanulate, apex acute; fused in basal 3.0 mm; persistent; tube about 5.0 mm long, 3.0 mm tall and 2.0 mm wide; lower cleft about 2.0 mm deep between lobes and upper and lower set; upper set of three fused to closer than 0.5 mm of apex;

Sepal color: Abaxial nearest RHS 144A with veins and dorsal portion exposed to intense sun blushed with nearest RHS 187A; adaxial base nearest RHS 145D;

Bracts: Each verticil subtended by two opposite bracts; apex acuminate, base truncate, shape nearly cordate; margin entire, ciliolate, and glabrous above and below; bract size up to 7.0 mm long and 5.0 mm wide, decreasing distally; color of both surfaces nearest RHS 145C with blushing and veins nearest RHS N186C;

Peduncles: Quadrangular in cross section, strong; mostly upright; flowering in peduncle up to 25 cm tall and 10.0 cm across; finely puberulent; heavily branched with opposite branches at about 45 degrees above horizontal at the three nodes below flowers; branches to about 10.0 cm long and 2.0 mm across; average space between verticils about 1.5 cm; about 330 flowers per inflorescence;

Peduncle color: Nearest RHS 138A in upper and lower regions;

Pedicels: Terete; puberulent; about 2.0 mm long and 0.5 mm diameter; horizontal to about 30 degrees above horizontal;

Pedicel color: Blend nearest RHS N77D;

Disease and pest resistance: Plants of *Salvia* 'Bumbleberry' perform best with adequate moisture and good drainage but are fairly drought tolerant once established; hardy from USDA zone 3 to 8; resistance to diseases and pests beyond that common to *Salvia* has not been noted;

It is claimed:

1. The new and distinct perennial *Salvia* plant named 'Bumbleberry' as herein described and illustrated useful for landscaping as a specimen plant, en masse or as a cut flower.

* * * * *